(12) United States Patent
Nakaoka et al.

(10) Patent No.: US 8,951,239 B2
(45) Date of Patent: Feb. 10, 2015

(54) DISPOSABLE DIAPER

(75) Inventors: Kenji Nakaoka, Osaka (JP); Yuki Takahashi, Mima-gun (JP)

(73) Assignee: Livedo Corporation, Ehime (JP)

( * ) Notice: Subject to any disclaimer, the term of this patent is extended or adjusted under 35 U.S.C. 154(b) by 215 days.

(21) Appl. No.: 13/808,719

(22) PCT Filed: Jul. 11, 2011

(86) PCT No.: PCT/JP2011/003964
§ 371 (c)(1),
(2), (4) Date: Jan. 7, 2013

(87) PCT Pub. No.: WO2012/008140
PCT Pub. Date: Jan. 19, 2012

(65) Prior Publication Data
US 2013/0110070 A1 May 2, 2013

(30) Foreign Application Priority Data

Jul. 14, 2010 (JP) .............................. P2010-159410

(51) Int. Cl.
*A61F 13/15* (2006.01)
(52) U.S. Cl.
USPC ............ 604/385.31; 604/385.24; 604/385.26; 604/385.25; 604/385.28; 604/385.16
(58) Field of Classification Search
USPC ............ 604/385.28, 385.24, 385.26, 385.25, 604/385.16, 385.31
See application file for complete search history.

(56) References Cited

U.S. PATENT DOCUMENTS

| | | | |
|---|---|---|---|
| 5,601,545 A | 2/1997 | Glaug et al. | |
| 5,624,424 A | 4/1997 | Saisaka et al. | |
| 6,369,291 B1 | 4/2002 | Uchimoto et al. | |
| 6,464,677 B1 * | 10/2002 | Noguchi et al. | ......... 604/385.27 |
| 6,508,798 B1 | 1/2003 | Widlund et al. | |

(Continued)

FOREIGN PATENT DOCUMENTS

| | | |
|---|---|---|
| CN | 1398174 | 2/2003 |
| CN | 1723000 | 1/2006 |

(Continued)

OTHER PUBLICATIONS

International Search Report issued Sep. 6, 2011 in International (PCT) Application No. PCT/JP2011/003964.

(Continued)

*Primary Examiner* — Jacqueline F. Stephens
(74) *Attorney, Agent, or Firm* — Wenderoth, Lind & Ponack, LLP (57) ABSTRACT

A disposable diaper has an absorbent body, an outer covering sheet and two end holding sheets, and both end portions of the absorbent body are fixed between the end holding sheets and the outer covering sheet. Since a turndown portion of an upper end portion of the end holding sheet is bonded on an upper end portion of a first covering sheet, a waist covering portion has structure where the first covering sheet is laminated on the two-layered end holding sheet. Therefore, a thickness of the outer covering sheet can be reduced, while maintaining strength of the waist covering portion by appropriately selecting material of the end holding sheet, thereby to easily improve softness of the disposable diaper. Since an upper end of a second covering sheet is positioned below the turndown portion, softness and breathability in an area between the turndown portion and the second covering sheet is increased.

14 Claims, 3 Drawing Sheets

(56) References Cited

U.S. PATENT DOCUMENTS

| | | |
|---|---|---|
| 7,347,847 B2 | 3/2008 | Toyoshima et al. |
| 2002/0035355 A1 | 3/2002 | Uchimoto et al. |
| 2003/0023219 A1 | 1/2003 | Nakaoka et al. |
| 2004/0039363 A1 | 2/2004 | Sugiyama et al. |
| 2004/0102757 A1 | 5/2004 | Olson |
| 2004/0108043 A1 | 6/2004 | Otsubo |
| 2005/0107763 A1 | 5/2005 | Matsuda et al. |
| 2011/0060305 A1 | 3/2011 | Otsubo |

FOREIGN PATENT DOCUMENTS

| | | |
|---|---|---|
| EP | 1 013 251 | 6/2000 |
| EP | 1 080 708 | 3/2001 |
| EP | 1 269 957 | 1/2003 |
| EP | 2 255 768 | 12/2010 |
| JP | 7-285187 | 10/1995 |
| JP | 2007-509725 | 4/2007 |
| JP | 2008-23116 | 2/2008 |
| JP | 4190132 | 12/2008 |
| JP | 2009-72532 | 4/2009 |
| TW | 345008 | 2/1984 |
| TW | 329663 | 8/1984 |
| WO | 99/62447 | 12/1999 |
| WO | 02/00154 | 1/2002 |

OTHER PUBLICATIONS

Patent Cooperation Treaty (PCT) Written Opinion of the International Searching Authority issued Sep. 6, 2011 in International (PCT) Application No. PCT/JP2011/003964.

* cited by examiner

DISPOSABLE DIAPER

TECHNICAL FIELD

The present invention relates to a pants-type disposable diaper which has a waist opening at an upper end and a pair of leg openings on a lower part.

BACKGROUND ART

A pants-type disposable diaper which has a waist opening at an upper end and a pair of leg openings on a lower part is conventionally used as one type of absorbent product for receiving excrement from a wearer (see Japanese Patent Application Laid-Open No. 2009-72532 (Document 1) and Japanese Parent Publication No. 4190132 (Document 2)).

In a disposable diaper disclosed in Document 1, an absorbent main body is bonded on an inner surface of an outer covering member having an inner layer sheet and an outer layer sheet, and an end portion of the absorbent main body in a longitudinal direction is covered with the inner layer sheet which is folded inward. Also in a disposable diaper disclosed in Document 2, an end portion of an absorbent main body in a longitudinal direction which is bonded on an inner surface of an outer covering member is covered with a covering sheet which is different from the outer covering member. The outer covering member has double-layered structure of an inner layer nonwoven fabric and an outer layer nonwoven fabric, and an end portion of the covering sheet in the longitudinal direction is covered with the outer layer nonwoven fabric which is folded inward.

Recently, in pants-type disposable diaper, comfort level of wearing a disposable diaper is progressively improved by thinning and softening of its outer covering sheet. On the other hand, in a pants-type disposable diaper, in order to prevent a portion in the vicinity of a waist opening, to cover a waist of a wearer (hereinafter, the portion is referred to as a "waist covering portion"), from being damaged by tension when putting the disposable diaper on the wearer, body pressure when the disposable diaper is worn, or the like, it is required to increase strength of the waist covering portion to a certain level.

In the disposable diaper disclosed in Document 1, a waist covering portion is formed by making the inner layer sheet of the outer covering member into double-layered structure. Since the inner layer sheet needs to be thickened for increasing strength of the waist covering portion, it is difficult to improve softness of the outer covering member while maintaining strength of the waist covering portion. In addition, in the disposable diaper disclosed in Document 2, a waist covering portion is formed by making the outer layer nonwoven fabric of the outer covering member into double-layered structure and locating the covering sheet therebetween. Thus, since mainly the outer layer nonwoven fabric needs to be thickened for increasing strength of the waist covering portion, it is not easy to improve softness of the outer covering member while maintaining strength of the waist covering portion.

SUMMARY OF INVENTION

The present invention is intended for a pants-type disposable diaper which has a waist opening at an upper end and a pair of leg openings on a lower part. It is a main object of the present invention to reduce a thickness of an outer covering sheet while maintaining strength of a waist covering portion, thereby to easily improve softness of the disposable diaper.

The disposable diaper according to the present invention comprises: an outer covering sheet having a front part, a back part and a middle part which are to be positioned on a front side, a back side and a crotch portion of a wearer; an absorbent body located on an inner surface of the outer covering sheet, the absorbent body lying from the front part to the back part via the middle part; and an end holding sheet bonded on an inner surface of an upper portion in one of the front part and the back part, the end holding sheet covering one end portion of the absorbent body in a longitudinal direction; wherein the outer covering sheet comprises: a first covering sheet; and a second covering sheet, laminated on an inner surface of the first covering sheet; an upper end portion of the end holding sheet has a turndown portion which is turned outward and downward, the turndown portion is bonded on an inner surface or an outer surface, of an upper end portion of the first covering sheet, and an upper end of the second covering sheet is positioned below the turndown portion.

In the present invention, it is possible to reduce a thickness of the outer covering sheet while maintaining strength of a waist covering portion, thereby to easily improve softness of the disposable diaper.

According to a preferred embodiment of the present invention, the turndown portion is bonded on the inner surface of the upper end portion of the first covering sheet. In this case, it is more preferable that the disposable diaper further comprises a waist elastic member bonded between the turndown portion and a portion of the end holding sheet which is opposed to the turndown portion, the waist elastic member contracting the end holding sheet and the first covering sheet to form waist gathers. Since the waist elastic member is bonded only to the end holding sheet, bonding of the waist elastic member can be easily performed when compared to the case where the waist elastic member is bonded between the end holding sheet and the outer covering sheet.

According to another preferred embodiment of the present invention, the first covering sheet is positioned outermost in the outer covering sheet, the end holding sheet and the first covering sheet are directly bonded to each other at a position between a lower end of the turndown portion and an upper end of the second covering sheet while a body-fitting elastic member is located between the end holding sheet and the first covering sheet, and the body-fitting elastic member comprises a plurality of body-fitting elastic elements arranged in an up-down direction, each of the plurality of body-fitting elastic elements being yarn-like or strip-like and extending in a left-right direction.

More preferably, the disposable, diaper further comprises another end holding sheet bonded on an inner surface of an upper portion in the other of the front part and the back part, the another end holding sheet covering the other end portion of the absorbent body in the longitudinal direction; wherein an upper end portion of the another end holding sheet has another turndown portion which is turned outward and downward, the another turndown portion is bonded on an inner surface or an outer surface of an upper end portion of the first covering sheet and an upper end of the second covering sheet is positioned below the another turndown portion. Therefore, in both the front part and the back part, the thickness of the outer covering sheet can be reduced while maintaining strength of the waist covering portion, thereby to easily improve softness of the disposable diaper.

These and other objects, features, aspects and advantages of the present invention will become more apparent from the following detailed description of the present invention when taken in conjunction, with the accompanying drawings.

DESCRIPTION OF EMBODIMENTS

Figure 1:
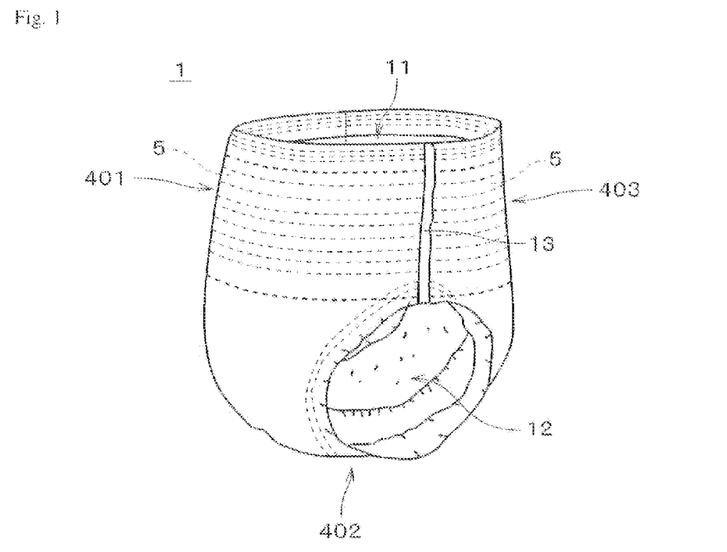
FIG. 1 is a perspective view showing an appearance of a disposable diaper.

FIG. 1 is a perspective view showing an appearance of a disposable diaper 1 in accordance with a preferred embodiment, of the present invention. As shown in FIG. 1, the disposable diaper 1 is a pants-type (i.e., pull-up type) diaper which has a waist opening 11 at an upper end being an end on the upper side of FIG. 1 and a pair of leg openings 12 on a lower part, and it receives excrement from a wearer.

Figure 2:
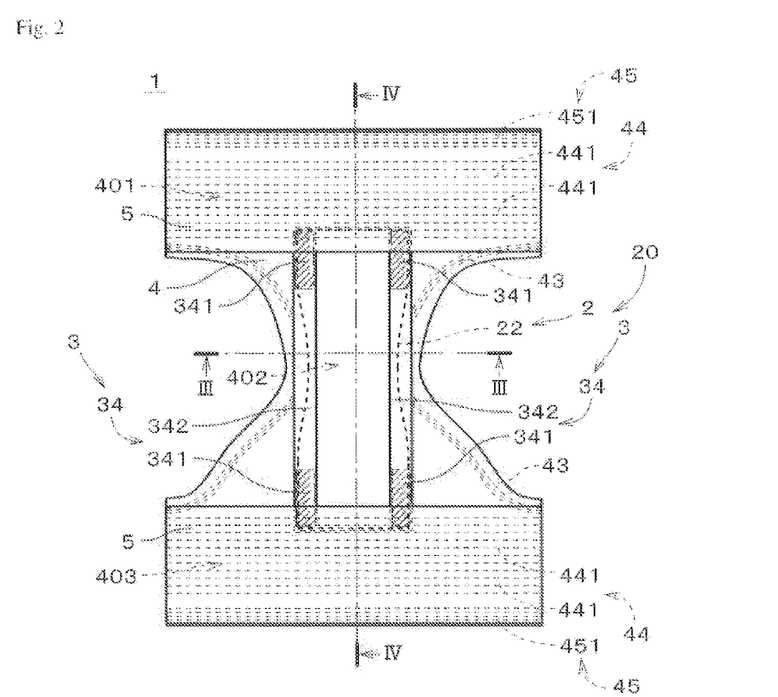
FIG. 2 is a plan view of the disposable diaper in a state where the disposable diaper is developed.

FIG. 2 is a plan view of the disposable diaper 1 in a state where the disposable diaper 1 is developed and in FIG. 2, the disposable diaper 1 is viewed from the wearer's side. As shown in FIG. 2, the disposable diaper 1 has an outer covering sheet 4, a sheet-like absorbent body (absorber) 20 which is attached on an inner surface (i.e., a surface to face the wearer) of the outer covering sheet 4 to absorb excrement from the wearer, and two end holding sheets 5 (they are sheet members and also called as "end sheets") which are bonded on the outer covering sheet 4 at both sides of the absorbent body 20 in a longitudinal direction (i.e., a vertical direction in FIG. 2). Each end holding sheet 5 is provided across almost the entire width of the outer covering sheet 4 with respect to a left-right direction of the disposable diaper 1 (i.e., a horizontal direction in FIG. 2). Respective end portions of the absorbent body 20 in the longitudinal direction are positioned (sandwiched) between the end holding sheets 5 and the outer covering sheet 4 to be fixed (held) therebetween.

In the disposable diaper 1, an upper portion in FIG. 2 is to be positioned on (to cover) the front side (stomach side) of the wearer, and a lower portion in FIG. 2 is to be positioned on the back side of the wearer. In the following description, the portions of the outer covering sheet 4 to be positioned on the front side and the back side of the wearer are referred to as a "front part 401" and a "back part 403", respectively, and a portion to face (to cover) the crotch portion of the wearer at a position between the front part 401 and the back part 403 is referred to as a "middle part 402". The middle part 402 is continuous with both the front part 401 and the back part 403. The absorbent body 20 lies from the front part 401 to the back part 403 via the middle part 402 in the outer covering sheet 4.

In manufacturing of the disposable diaper 1, the outer covering sheet 4 is folded at the middle part 402 together with the absorbent body 20. In the state where the middle part 402 is located on the downside, inner surfaces at left and right ends of the front part 401 are indirectly bonded to inner surfaces at left and right ends of the back part 403, respectively, via the two end holding sheets 5 in the front side and the back side by heat bonding (heat-sealing) under heating and pressing. In other words, respective end holding sheets 5 are bonded on the inner surfaces of the front part 401 and the back part 403 in the outer covering sheet 4, and inner surfaces of the two end holding sheets 5 are directly bonded on each other at left and right ends thereof by heat bonding. As above, since the inner surfaces of the both side ends of the front part 401 are bonded to the inner surfaces of the both side ends of the back part 403, respectively, as shown in FIG. 1, the waist opening 11 is formed at upper ends of the front part 401 and the back part 403, and the pair of leg openings 12 lying in left and right of the middle part 402 is formed under the front part 401 and the back part 403. In addition, strip-like side seal parts 13 protruding from the outer surface of the disposable diaper 1 are formed on left and right side portions of the disposable diaper 1, and the side seal parts 13 lie from the waist opening 11 to the leg openings 12. In FIG. 1, one leg opening 12 of the pair of leg openings 12 and one side seal part 13 of the pair of side seal parts 13 are drawn.

Figure 3:
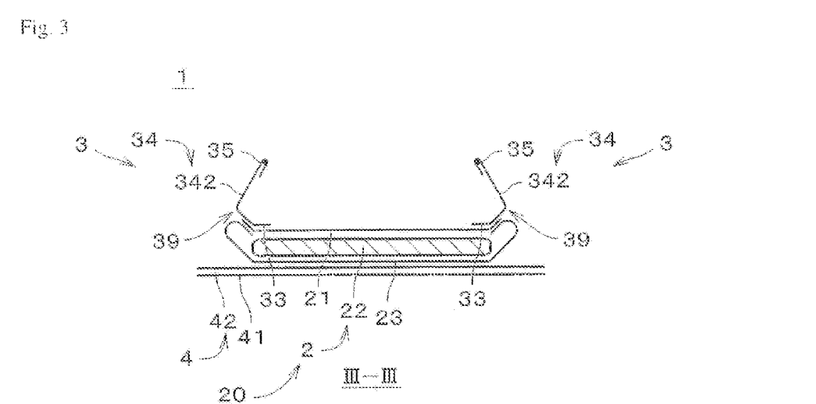
FIG. 3 is a cross-sectional view of the disposable diaper.

FIG. 3 is a cross-sectional view of the disposable diaper 1 taken along a line III-III in FIG. 2 (cross-sectioned at the middle part 402). In FIG. 3, respective constituents of the disposable diaper 1 are drawn so as to be slightly apart from one another for the convenience of illustration (the same applies to FIG. 4). As shown in FIGS. 2 and 3, the absorbent body 20 has a sheet-like main body part 2 and a pair of side sheets 3 located on both side portions of the main body part 2 (i.e., both end portions of the main body part 2 in the left-right direction), and the pair of side sheets 3 extends across almost the entire length of the main body part 2 in the longitudinal direction. As shown in FIG. 3, the main body part 2 has a top sheet 21, a back sheet 23 and an absorbent core 22 which is located between the top sheet 21 and the back sheet 23. The contour of the absorbent core 22 is drawn by thick broken lines in FIG. 2 for easy understanding of the drawing.

As shown in FIG. 2, a width of the absorbent core 22 at each end portion in the longitudinal direction is larger than that at a middle portion in the rise longitudinal direction. In other words, the absorbent core 22 is formed in a form of hourglass. The back sheet 23 shown in FIG. 3 is bonded on the outer covering sheet 4 with hot melt adhesive or the like, to fix the absorbent body 20 on the outer covering sheet 4.

Each side sheet 3 has a strip-like bonded part 33 and a side wall part 34. The bonded part 33 is one of two portions divided by a folding line 39 extending across almost the entire length thereof in the longitudinal direction and the bonded part 33 is positioned on the main body part 2. The side wall part 34 is the other of the two portions. The bonded part 33 is located in the vicinity of the side edge of the main body part 2, it lies across almost the entire length thereof in the longitudinal direction, and it is bonded on the upper side (i.e., the wearers side) of the main body part 2 with hot melt adhesive. The side wall part 34 is continuous from the bonded part 33 via an outer edge, which is the folding line 39, of the bonded part 33 in the left-right direction. The pair of side wall parts 34 lies on left and right side portions of the main body part 2 and extends across almost the entire length of the main body part 2 in the longitudinal direction.

In both end portions of each side wall part 34 in the longitudinal direction, the side wall part 34 is laid on the bonded part 33 and fixed on the bonded part 33 by heat bonding, ultrasonic bonding or bonding with hot melt adhesive or the like. In the following description, each portion of the side wall part 34 which is fixed on the bonded part 33 is referred to as a "side wall end part 341", and in FIG. 2, hatching lines are drawn at each side wall end part 341 of the side sheet 3 for easy understanding of the drawing. As shown in FIGS. 2 and 3, each side wall part 34 has a standing part 342 standing upward from the main body part 2 at a middle portion thereof in the longitudinal direction, and the standing part 342 is continuous with two side wall end parts 341. In the side wall part 34 shown in FIG. 3, an elastic member 35 is bonded on a free edge of the standing part 342, and gathers are formed in the standing part 342 by contraction of the elastic member 35.

Figure 4:
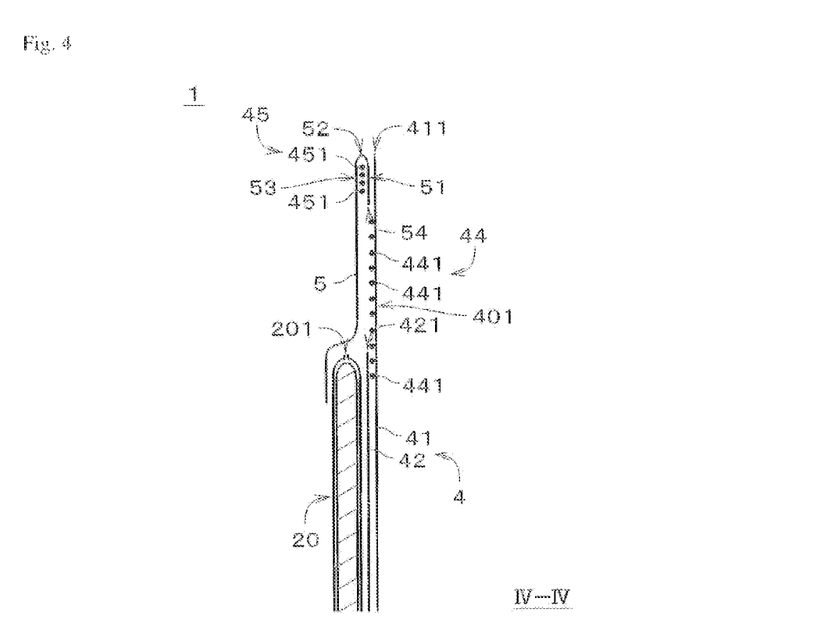
FIG. 4 is a cross-sectional view of the disposable diaper.

FIG. 4 is a cross-sectional view of the disposable diaper 1 taken along a line IV-IV in FIG. 2. FIG. 4 shows the front side of the disposable diaper 1. As shown in FIGS. 3 and 4, the outer covering sheet 4 has a first covering sheet 41 and a second covering sheet 42, and the second covering sheet 42 is laminated (layered) on an inner surface (i.e., a surface to face the wearer) of the first covering sheet 41 to be directly bonded thereon. The first covering sheet 41 is positioned outermost in the outer covering sheet 4, and the second covering sheet 42 is positioned innermost in the outer covering sheet 4. As shown in FIG. 4, an upper end 421 of the second covering sheet 42 is positioned below an upper end 411 of the first covering sheet 41 (i.e., a distance between the upper end 421 and the waist opening 11 is more than a distance between the upper end 411 and the waist opening 11), and the upper end 421 is overlapped with an upper end 201 of the absorbent body 20 or is positioned between the upper end 411 of the first covering sheet 41 and the upper end 201 of the absorbent body 20.

The end holding sheet 5 is bonded on an inner surface of an upper portion in the front part 401 of the outer covering sheet 4 while the end holding sheet 5 covers one end portion (front end portion) of the absorbent body 20 in the longitudinal direction. An upper end portion of the end holding sheet 5 has a turndown portion 51 which is turned (folded back) outward (i.e., toward a direction away from the wearer) and downward. An upper end 52 of the turndown portion 51 (i.e., a folding line of the end holding sheet 5) is positioned slightly below the upper end 411 of the first coveting sheet 41, and the upper end 421 of the second covering sheet 42 is positioned below a lower end 54 of the turndown portion 51. A width of the turndown portion 51 in an up-down direction (i.e., the width is a distance in the up-down direction between the upper end 52 and the lower end 54 of the turndown portion 51) is preferably equal to or greater than 1 centimeter (cm) and equal to or less than 8 centimeter (more preferably, equal to or greater than 3 centimeter and equal to or less than 6 centimeter). The turndown portion 51 is bonded on an inner surface of an upper end portion of the first covering sheet 41 with hot melt adhesive or the like.

A waist elastic member 45 is bonded between the turndown portion 51 and a portion 53 of the end holding sheet 5 which is opposed to the turndown portion 51, with hot melt adhesive or the like. The waist elastic member 45 has a plurality of waist elastic elements 451 arranged in the up-down direction. As shown in FIG. 2, each of the plurality of waist elastic elements 451 is yarn-like or strip-like and extends in the left-right direction. In the disposable diaper 1, since the end holding sheet 5 and the first covering sheet 41 are contracted by contraction of the waist elastic member 45, waist gathers to be positioned on the waist of the wearer are formed in the front side of the disposable diaper 1.

As shown in FIG. 4, between the lower end 54 of the turndown portion 51 of the end holding sheet 5 and the upper end 421 of the second covering sheet 42, the end holding sheet 5 and the first covering sheet 41 are bonded to each other with hot melt adhesive or the like. Between the lower end 54 of the turndown portion 51 of the end holding sheet 5 and the upper end 421 of the second covering sheet 42, and below the upper end 421 of the second covering sheet 42, a body-fitting elastic member (hip-encircling elastic member) 44 is located and bonded on the end holding sheet 5 and the first covering sheet 41 or the second covering sheet 42 and the first covering sheet 41 with hot melt adhesive or the like. In other words, between the lower end 54 of the turndown portion 51 and the upper end 421 of the second covering sheet 42, the end holding sheet 5 and the first covering sheet 41 are directly bonded to each other while the body-fitting elastic member 44 is sandwiched (located) between the end holding sheet 5 and the first covering sheet 41. The body-fitting elastic member 44 has a plurality of body-fitting elastic elements 441 arranged in the up-down direction at each of an area lying above the upper end 421 of the second covering sheet 42 and an area lying below the upper end 421 of the second covering sheet 42. As shown in FIG. 2, each of the plurality of body-fitting elastic elements 441 is yarn-like or strip-like and extends in the left-right direction. In the disposable diaper 1, since the end holding sheet 5, the first covering sheet 41 and the second covering sheet 42 are contracted by contraction of the body-fitting elastic member 44, hip gathers to be positioned on the body (hip) of the wearer are formed in the front side of the disposable diaper 1.

Structure of the back side of the disposable diaper 1 is same as the structure of the front side shown in FIG. 4. That is, another end holding sheet 5 whose upper end portion has a turndown portion 51 is bonded on an inner surface of an upper portion in the back part 403 (see FIG. 2) of the outer covering sheet 4 while covering the other end portion (back end portion) of the absorbent body 20 in the longitudinal direction. An upper end 421 of the second covering sheet 42 is positioned below a lower end 54 of the turndown portion 51. In a similar fashion to the front side, in the back side of the disposable diaper 1, the end holding sheet 5 and the first covering sheet 41 are contracted by contraction of a waist elastic member 45, thereby to form waist gathers, and the end holding sheet 5, the first covering sheet 41 and the second covering sheet 42 are contracted by contraction of a body-fitting elastic member 44, thereby to form hip gathers.

The top sheet 21 is made of liquid-pervious sheet material, and the top sheet 21 immediately catches moisture of excrement from the wearer and moves the moisture into the absorbent core 22. For example, the top sheet 21 is a liquid-pervious nonwoven fabric (e.g., a point-bond nonwoven fabric, air-through nonwoven fabric, spunbond nonwoven fabric or the like) made of hydrophobic fibers (polypropylene, polyethylene, polyester, polyamide, nylon or the like) where hydrophilic treatment is performed on its surface with a surfactant. A nonwoven fabric (for example, spunlace nonwoven fabric) made of hydrophilic fibers such as cellulose, rayon, cotton may be used as the top sheet 21.

The absorbent core 22 is formed by wrapping a mixture of hydrophilic fibers such as crushed pulp fibers or cellulose fibers and super absorbent material such as granulated super absorbent polymers (e.g., SAP (Super Absorbent Polymer)) or super absorbent fibers, in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap tire hydrophilic fibers, is bonded to the hydrophilic fibers and the absorbent material with hot melt adhesive, to prevent deformation of the hydrophilic fibers and falling of the absorbent material (especially, falling after absorption of moisture). In the present embodiment, the absorbent core 22 includes pulp fibers and SAP.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers, or a water-repellent or liquid-impervious plastic film. The back sheet 23 prevents moisture of excrement or the like which has come to the back sheet 23, from leaking out to the outside of the main body part 2. In a case where a plastic film is used for the back sheet 23, it is preferable that a plastic film with permeability (breathability) is used, from the view point of preventing sweatiness in the disposable diaper 1 and providing comfortable feeling to the wearer.

As a sheet main body of the side sheet 3, used is a water-repellent or liquid-impervious nonwoven fabric (for example, a spunbond nonwoven fabric, meltblown nonwoven fabric or SMS nonwoven fabric) made of hydrophobic fibers. As the elastic member 35, for example, a polyurethane yarn, strip-like polyurethane film, yarn-like or strip-like natural rubber, or the like is used. In the present embodiment, a polyurethane yarn is used as the elastic member 35. As the end holding sheet 5, a nonwoven fabric made of hydrophobic fibers is used.

As the first covering sheet 41 and the second covering sheet 42 of the outer covering sheet 4, used is a water-repellent or liquid-impervious nonwoven fabric made of hydrophobic fibers, or a water-repellent or liquid-impervious plastic film in a similar fashion to the back sheet 23. A laminated sheet of the nonwoven fabric and the plastic film may be used. It is preferable that the plastic film has permeability (breathability), In a similar fashion to the top sheet 21, a nonwoven fabric made of hydrophilic fibers or a liquid-pervious nonwoven fabric made of hydrophobic fibers where hydrophilic treatment is performed may be utilized as the first covering sheet 41 and the second covering sheet 42. As each elastic element of the leg elastic member 43, the body-fitting elastic member 44 and the waist elastic member 45, for example, a polyurethane yarn, strip-like polyurethane film, yarn-like or strip-like natural rubber, or the like is used in a similar fashion to the elastic member 35 of the side sheet 3. In the present embodiment, polyurethane yarns are utilized as the elastic elements.

In a pants-type disposable diaper, in order to prevent a portion in the vicinity of a waist opening 11, to cover (surround) a waist of a wearer (hereinafter, the portion is referred to as a "waist covering portion"), from being damaged by tension when putting the disposable diaper on the wearer, body pressure when the disposable diaper is worn, or the like, it is required to increase strength of the waist covering portion to a certain level.

In the front side of the disposable diaper 1 in accordance with the present embodiment, as described above, the turndown portion 51 is formed in the upper end portion of the end holding sheet 5, the turndown portion 51 is bonded on the upper end portion of the first covering sheet 41, and therefore a waist covering portion has structure where the first covering sheet 41 which is one layer is laminated on the two-layered end holding sheet 5. Therefore, increase in strength of the waist covering portion by increase in strength of the end holding sheet 5 at a rate is more than that by increase in strength of the first covering sheet 41 at the same rate. Thus, a thickness of the first covering sheet 41 can be easily reduced while maintaining strength of the waist covering portion by appropriately selecting material of the end holding sheet 5, for example, by increasing a weight per unit area in the end holding sheet 5. As the result, it is possible to reduce the thickness of the outer covering sheet 4, thereby to easily improve softness of the disposable diaper 1 (to easily perform improvement of softness of the disposable diaper 1). In particular, softness of portions, to surround the legs of the wearer, at which only the outer covering sheet 4 is located as a sheet member to cover skin of the wearer is further improved in the disposable diaper 1.

Since the upper end 421 of the second covering sheet 42 is positioned below the turndown portion 51 of the end holding sheet 5, sheet members to cover skin of the wearer consist of the end holding sheet 5 which is one layer and the first covering sheet 41 whose thickness can be reduced as described above, in an area between the lower end 54 of the turndown portion 51 and the upper end 421 of the second covering sheet 42. Therefore, softness and breathability in the area is increased and comfort level of wearing the disposable diaper 1 is improved. Furthermore, since a distance between the lower end 54 of the turndown portion 51 and the upper end 421 of the second covering sheet 42 is increased so as to be able to locate the plurality of body-fitting elastic elements 441, breathability of the disposable diaper 1 is further increased, thereby to further improve comfort level of wearing the disposable diaper 1.

In the back side of the disposable diaper 1, in a similar fashion to the front side, since the turndown portion 51 formed in the upper end portion of the end holding sheet 5 is bonded on the upper end portion of the first covering sheet 41, the thickness of the first coveting sheet 41 can be reduced while maintaining strength of the waist covering portion by appropriately selecting material of the end holding sheet 5. As the result, it becomes easy to improve softness of the disposable diaper 1 by reducing the thickness of the outer covering sheet 4. In addition, since a distance between the upper end 421 of the second covering sheet 42 positioned below the turndown portion 51 and the lower end 54 of the turndown portion 51 is increased so as to be able to locate the plurality of body-fitting elastic elements 441, softness and breathability of the area between the lower end 54 of the turndown portion 51 and the upper end 421 of the second covering sheet 42 are increased, thereby to improve comfort level of wearing the disposable diaper 1.

As above, since each of the front and back end holding sheets 5 is provided across almost the entire width of the outer covering sheet 4, the inner surfaces of the front and back end holding sheets 5 are heat-bonded to each other directly to form the pair of side seal parts 13. Thus, it is only necessary that heat bondable fibers are contained in the end holding sheet 5, and it is not necessary that heat bondable fibers are contained in the outer covering sheet 4. Thus, freedom of material selection for the outer covering sheet 4 can be increased. In the disposable diaper 1, since the area of the outer covering sheet 4 is larger than the area of the end holding sheet 5, by increase of freedom of material selection for the outer covering sheet 4, reduction of material cost for the disposable diaper 1 can be easily achieved.

In a general apparatus for manufacturing a disposable diaper, it is not easy to apply hot melt adhesive to the very vicinity of an edge of a sheet member. Thus, when the sheet member is attached on another member or the like, a portion of the sheet member lying in the vicinity of the edge is not attached thereon, and there may be a case where the portion is caught somewhere and damaged when the disposable diaper is packed or worn, or to put the disposable diaper on a wearer smoothly is disturbed. There also may be a case where comfort level of wearing the disposable diaper is decreased because the portion comes in contact with skin of the wearer in the state where it is bent or wrinkled. Furthermore, since an end portion which is not attached is visible, an appearance of the disposable diaper may become worse.

However, in the disposable diaper 1 in accordance with the present embodiment, the turndown portion 51 or the end holding sheet 5 is bonded on the inner surface of the first covering sheet 41. In other words, the turndown portion 51 is positioned between the portion 53 of the end holding sheet 5 which is opposed to the turndown portion 51 and the first covering sheet 41. Therefore, even if hot melt adhesive is not applied to the vicinity of the lower end 54 of the turndown portion 51, a portion of the turndown portion 51 lying in the vicinity of the lower end 54 is prevented from being caught somewhere and damaged, and to put the disposable diaper 1 on the wearer smoothly is not disturbed. It is also prevented that comfort level of wearing the disposable diaper is decreased due to direct contact between the portion and skin of the wearer, and the appearance of the disposable diaper 1 can be prevented from becoming worse due to the portion.

Furthermore, in the disposable diaper 1, the waist elastic member 45 is bonded between the turndown portion 51 of the end holding sheet 5 and the portion 53 which is opposed to the turndown portion 51. In other words, the turndown portion 51 and the portion 53 opposed to the turndown portion 51 are directly bonded to each other while the waist elastic member 45 is located between the turndown portion 51 and the portion 53. As above, since the waist elastic member 45 is bonded only to the end holding sheet 5, bonding of the waist elastic member 45 can be easily performed when compared to the case where the waist elastic member 45 is bonded between the end holding sheet 5 and the outer covering sheet 4.

In the end holding sheet 5, since the width of the turndown portion 51 in the up-down direction is equal to or greater than 1 centimeter (more preferably, equal to or greater than 3 centimeter), the width of the waist covering portion in the up-down direction becomes sufficiently large and a portion in the vicinity of the waist opening 11 is more surely prevented from being damaged by tension when putting the disposable diaper on the wearer, body pressure when the disposable diaper is worn, or the like. Since the width of the turndown portion 51 in the up-down direction is equal to or less than 8 centimeter (more preferably, equal to or less than 6 centimeter), an area with high breathability which is positioned between the turndown portion 51 and the second covering sheet 42 becomes large and comfort level of wearing the disposable diaper 1 can be further improved.

Though the preferred embodiments of the present invention have been discussed above, the present invention is not limited to the above-discussed preferred embodiments, but allows various variations.

Figure 5:
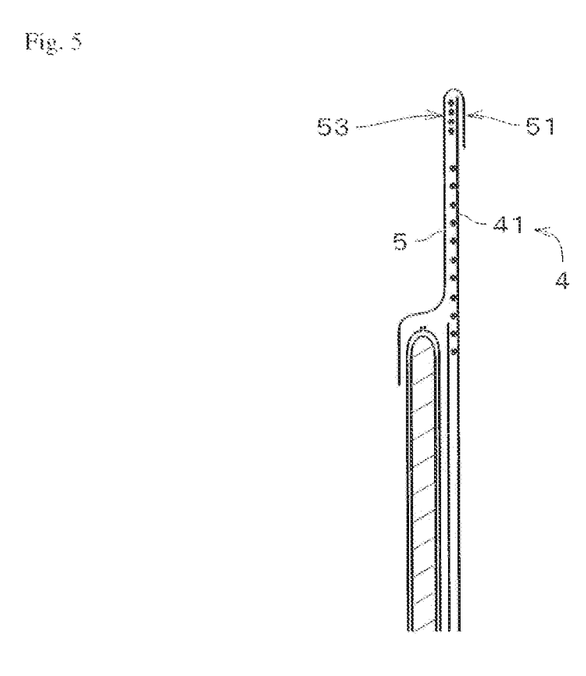
FIG. 5 is a cross-sectional view showing another example of disposable diaper.

For example, as shown in FIG. 5, the turndown portion 51 of the end holding sheet 5 may be bonded on an outer surface of the upper end portion of the first covering sheet 41. In other words, the upper end portion of the first covering sheet 41 is bonded so as to be positioned (sandwiched) between the turndown portion 51 of the end holding sheet 5 and the portion 53 opposed to the turndown portion 51. In this case, while maintaining strength of the portion to cover the waist of the wearer by appropriately selecting material for the end holding sheet 5, the thickness of the outer covering sheet 4 is reduced, thereby to easily improve softness of the disposable diaper.

The outer covering sheet 4 may have structure where three or more sheet members are stacked. However, in the disposable diaper in accordance with the above preferred embodiments, more preferably, only the first covering sheet 41 positioned outermost in the outer covering sheet 4 and the second covering sheet 42 positioned innermost are provided as sheet members. Therefore, softness and breathability of the area positioned between the lower end 54 of the turndown portion 51 and the upper end 421 of the second covering sheet 42 are increased and structure of the outer covering sheet 4 is simplified.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST 1 disposable diaper
4 outer covering sheet
5 end holding sheet
11 waist opening
12 leg opening
20 absorbent body
41 first covering sheet
42 second covering sheet
44 body-fitting elastic member
45 waist elastic member
51 turndown portion
53 portion
54 lower end
401 front part
402 middle part
403 back part
421 upper end
441 body-fitting elastic element

The invention claimed is:

1. A pants-type disposable diaper which has a waist opening at an upper end and a pair of leg openings on a lower part, comprising:
    an outer covering sheet having a front part, a back part and a middle part which are to be positioned on a front side, a back side and a crotch portion of a wearer;
    an absorbent body located on an inner surface of said outer covering sheet, said absorbent body lying from said front part to said back part via said middle part; and
    an end holding sheet bonded on an inner surface of an upper portion in one of said front part and said back part, said end holding sheet covering one end portion of said absorbent body in a longitudinal direction; wherein
    said outer covering sheet comprises:
    a first covering sheet; and
    a second covering sheet laminated on an inner surface of said first covering sheet;
    an upper end portion of said end holding sheet has a turndown portion which is turned outward and downward, said turndown portion is bonded on an inner surface or an outer surface of an upper end portion of said first covering sheet, and
    an upper end of said second covering sheet is positioned below said turndown portion.

2. The disposable diaper according to claim 1, wherein said turndown portion is bonded on said inner surface of said upper end portion of said first covering sheet.

3. The disposable diaper according to claim 2, further comprising
    a waist elastic member bonded between said turndown portion and a portion of said end holding sheet which is opposed to said turndown portion, said waist elastic member contracting said end holding sheet and said first covering sheet to form waist gathers.

4. The disposable diaper according to claim 3, wherein said first covering sheet is positioned outermost in said outer covering sheet,
    said end holding sheet and said first covering sheet are directly bonded to each other at a position between a lower end of said turndown portion and an upper end of said second covering sheet while a body-fitting elastic member is located between said end holding sheet and said first covering sheet, and said body-fitting elastic member comprises a plurality of body-fitting elastic elements arranged in an up-down direction, each of said plurality of body-fitting elastic elements being yarn-like or strip-like and extending in a left-right direction.

5. The disposable diaper according to claim 4, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and an upper end of said second covering sheet is positioned below said another turndown portion.

6. The disposable diaper according to claim 3, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and an upper end of said second covering sheet is positioned below said another turndown portion.

7. The disposable diaper according to claim 2, wherein said first covering sheet is positioned outermost in said outer covering sheet, said end holding sheet and said first covering sheet are directly bonded to each other at a position between a lower end of said turndown portion and an upper end of said second covering sheet while a body-fitting elastic member is located between said end holding sheet and said first covering sheet, and said body-fitting elastic member comprises a plurality of body-fitting elastic elements arranged in an up-down direction, each of said plurality of body-fitting elastic elements being yarn-like or strip-like and extending in a left-right direction.

8. The disposable diaper according to claim 7, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and an upper end of said second covering sheet is positioned below said another turndown portion.

9. The disposable diaper according to claim 2, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and an upper end of said second covering sheet is positioned below said another turndown portion.

10. The disposable diaper according to claim 1, wherein said first covering sheet is positioned outermost in said outer covering sheet, said end holding sheet and said first covering sheet are directly bonded to each other at a position between a lower end of said turndown portion and an upper end of said second covering sheet while a body-fitting elastic member is located between said end holding sheet and said first covering sheet, and said body-fitting elastic member comprises a plurality of body-fitting elastic elements arranged in an up-down direction, each of said plurality of body-fitting elastic elements being yarn-like or strip-like and extending in a left-right direction.

11. The disposable diaper according to claim 10, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and an upper end of said second covering sheet is positioned below said another turndown portion.

12. The disposable diaper according to claim 1, wherein a width of said turndown portion in an up-down direction is equal to or greater than 1 centimeter and equal to or less than 8 centimeter.

13. The disposable diaper according to claim 12, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and an upper end of said second covering sheet is positioned below said another turndown portion.

14. The disposable diaper according to claim 1, further comprising another end holding sheet bonded on an inner surface of an upper portion in the other of said front part and said back part, said another end holding sheet covering the other end portion of said absorbent body in said longitudinal direction; wherein an upper end portion of said another end holding sheet has another turndown portion which is turned outward and downward, said another turndown portion is bonded on an inner surface or an outer surface of an upper end portion of said first covering sheet, and
an upper end of said second covering sheet is positioned below said another turndown portion.

* * * * *